(12) United States Patent
Faroon et al.

(10) Patent No.: US 12,216,132 B2
(45) Date of Patent: Feb. 4, 2025

(54) METHOD FOR DISINFECTION AND FUNCTION CONTROL OF A CHLORINE SENSOR

(71) Applicant: VIVONIC GMBH, Sailauf (DE)

(72) Inventors: Yahya Faroon, Greven (DE); Jürgen Schwerdhöfer, Marktheidenfeld (DE)

(73) Assignee: VIVONIC GMBH, Sailauf (DE)

( * ) Notice: Subject to any disclaimer, the term of this patent is extended or adjusted under 35 U.S.C. 154(b) by 279 days.

(21) Appl. No.: 17/789,616

(22) PCT Filed: Dec. 17, 2020

(86) PCT No.: PCT/EP2020/086869
§ 371 (c)(1),
(2) Date: Jun. 28, 2022

(87) PCT Pub. No.: WO2021/136680
PCT Pub. Date: Jul. 8, 2021

(65) Prior Publication Data

US 2023/0036931 A1    Feb. 2, 2023

(30) Foreign Application Priority Data

Dec. 30, 2019   (DE) .................... 10 2019 135 883.3

(51) Int. Cl.
| | | |
|---|---|---|
| *G01N 35/00* | (2006.01) | |
| *A61L 2/18* | (2006.01) | |
| *G01N 33/18* | (2006.01) | |
| *A61L 101/08* | (2006.01) | |
| *C02F 1/00* | (2023.01) | |
| *C02F 103/04* | (2006.01) | |

(52) U.S. Cl.
CPC .......... *G01N 35/00693* (2013.01); *A61L 2/18* (2013.01); *G01N 33/18* (2013.01); *A61L 2101/08* (2020.08); *C02F 1/008* (2013.01); *C02F 2103/04* (2013.01); *C02F 2209/29* (2013.01); *C02F 2303/14* (2013.01)

(58) Field of Classification Search
CPC ............ G01N 35/00693; G01N 33/18; G01N 33/0006; G01N 33/007; G01N 2033/0072; A61L 2/18; A61L 2101/08; A61L 2202/11; C02F 1/008; C02F 2103/04; C02F 2209/29; C02F 2303/14; C02F 1/76; C02F 2103/026; C02F 2303/185; C02F 2303/20
USPC ...... 73/1.02, 1.03, 1.06, 1.07, 19.1; 134/2, 3, 134/22.1–23, 26, 31, 41, 56 R, 57 R, 134/58 R, 113, 166, 167, 168, 169, 171
See application file for complete search history.

(56) References Cited

U.S. PATENT DOCUMENTS

| | | |
|---|---|---|
| 6,174,419 B1 | 1/2001 | Akiyama |
| 2004/0211731 A1 | 10/2004 | Ferguson et al. |
| 2016/0095475 A1* | 4/2016 | Brennan ................. A23N 12/02 134/18 |

FOREIGN PATENT DOCUMENTS

| | | |
|---|---|---|
| DE | 10 2007 014 213 A1 | 9/2008 |
| DE | 10 2013 011 746 A1 | 1/2015 |

(Continued)

*Primary Examiner* — Robert R Raevis
(74) *Attorney, Agent, or Firm* — Jacobson Holman PLLC (57) ABSTRACT

A method for the disinfection and/or function control of a chlorine sensor, which is preferably used in water conditioning for medical or pharmaceutical purposes, employs a chlorine-containing solution different from a measurement solution being specifically supplied to the chlorine sensor at time intervals.

20 Claims, 3 Drawing Sheets

(56) References Cited

FOREIGN PATENT DOCUMENTS

| | | |
|---|---|---|
| DE | 10 2013 011 751 A1 | 1/2015 |
| DE | 10 2013 011 752 A1 | 1/2015 |
| DE | 10 2017 214 810 A1 | 2/2019 |
| EP | 1 108 683 A2 | 6/2001 |
| EP | 2 824 079 A1 | 1/2015 |

* cited by examiner

METHOD FOR DISINFECTION AND FUNCTION CONTROL OF A CHLORINE SENSOR

The present invention relates to a method for the disinfection and functional monitoring of a chlorine sensor that is preferably used as part of water conditioning for medical or pharmaceutical purposes.

In the medical or pharmaceutical sector, chlorine sensors by means of which it is to be ensured that the conditioned water is chlorine-free or at least very largely chlorine-free before the water is, for example, supplied to a treatment machine for treating a patient as part of dialysis are used in the context of water conditioning (e.g. production of dialysis water, ultrapure water, or RO water). Chlorine is in this process frequently removed from the incoming water in a prefiltering unit before it is supplied to the purification filter stage (such as a reverse osmosis filter stage) of a water conditioning plant since some components of the purification filter stage react sensitively to certain amounts of chlorine and can even be damaged thereby.

Unlike other applications of chlorine sensors (e.g. in swimming pools), the special feature of this application comprises the chlorine sensors used always only reporting the absence of chlorine since the chlorine has already been removed from the water in regular operation by means of the filter, e.g. an active carbon filter, connected upstream of the chlorine sensor.

As a rule, such a chlorine sensor thus reports the absence of chlorine.

This brings about the problem that due to the absence of chlorine in the water bacteria can, for example, form a biofilm on the chlorine sensor, whereby the hygiene of the water conditioning plant and also the operability of the sensor are impaired. A biofilm can thus, for example, cover a membrane at a sensor chamber and thereby reduce the permeability of this membrane. This can in turn reduce the sensitivity of the sensor, increase the response time or—in the case of an ion-selectively measuring sensor—falsify the measured ion concentrations.

It is additionally only possible with difficulty to monitor the function of the chlorine sensor. If such a sensor should lose its measuring capability (e.g. because the medium to be measured does not spatially move to where the sensor measures), the signal applied in this case would not be distinguishable from normal operation. The absence of chlorine is measured in both cases. This would be fatal in the event that water containing chlorine or the medium simply does not reach the active measurement zone of the sensor. It would, however, also be difficult on a different failure of the sensor to determine it on the basis of the measured signal. In view of the fact that the sensor outputs a signal corresponding to the measured value "No chlorine content" in normal operation, a measured value for "No chlorine content" may likewise be applied on a failure of the measuring capability of the sensor. In other words, a signal applied in the event of a defect of the sensor can only be distinguished with difficulty from a desired "silence" of the functional sensor due to the absence of chlorine in a regular event.

It is thus the underlying object of the present invention to alleviate or even to fully eliminate the problems known in the prior art. It is specifically the underlying object of the present invention to in particular ensure a reliable disinfection and/or a functional monitoring with a chlorine sensor that is used in the medical/pharmaceutical sector.

This object is achieved by the methods in accordance with the independent claims. The dependent claims relate to advantageous further developments of the invention.

The basic idea underlying the present invention is to directly supply a solution containing chlorine to a sensor described in the introduction to compensate the disadvantages of the absence of chlorine in the measurement solution or in the water.

An aspect of the present invention relates to a method for the disinfection of a chlorine sensor that is preferably used as part of water conditioning for medical or pharmaceutical purposes, the method comprising the steps:

providing a starting solution containing chlorine that is provided separately from a measurement solution whose chlorine content the chlorine sensor detects;

diluting the starting solution containing chlorine to a desired degree; and supplying the diluted starting solution containing chlorine to the chlorine sensor.

The diluted starting solution containing chlorine preferably remains in/at the chlorine sensor for a suitable dwell time or exposition time. The chlorine sensor is thus exposed to the chlorine content of the diluted starting solution containing chlorine during the exposition time. The exposition time can vary between only a few seconds and a plurality of minutes.

The exposition time preferably amounts to between approximately 1 minute and approximately 10 minutes preferably between 2 minutes and 8 minutes, in particular between 3 minutes and 7 minutes, particularly between 4 and 6 minutes. The exposition time amounts to approximately 5 minutes in accordance with a preferred embodiment.

A shorter exposition time is also conceivable, e.g. a time between 10 seconds and 1 minute, for example approximately 30 seconds, etc. is conceivable as is a longer time such as 10 to 15 minutes.

The present method differs from a conventional method using a flow of a fluid continuously applied to a sensor by the provision of an adjustable and predeterminable exposition time.

The tank for providing/storing the starting solution containing chlorine can be kept as small as possible by the dilution step.

The concentration of the solution ultimately being used for the disinfection can furthermore be set flexibly by means of the dilution step and can thus e.g. be adapted to the sensitivity of a sensor, in particular also of a sensor optimized to the recognition of very small amounts of chlorine.

If the disinfection should be carried out as quickly as possible with only a small dwell time of the diluted starting solution containing chlorine in the chlorine sensor, a relatively high chlorine concentration can, for example, be set in the dilution step.

If, on the other hand, the emphasis is on a more gentle disinfection, a stronger dilution and thus a relatively low chlorine concentration can be set, for example, in the dilution step. Damage to system components of e.g. an ultrapure water conditioning plant coming into contact with the chlorine can be particularly advantageously minimized by a greater dilution.

It has proved to be advantageous in practice for the method to further comprise the step:

removing the diluted starting solution containing chlorine from the chlorine sensor, preferably by flushing the chlorine sensor, preferably using a fluid low or high in chlorine.

This step ensures that the diluted starting solution containing chlorine is removed from the chlorine sensor after the elapse of the desired exposition time.

The service life of the chlorine sensor and possibly of further components of a chlorine sensor device can be extended by the removal of the diluted starting solution containing chlorine from the chlorine sensor after it has developed its desired effect at the chlorine sensor. A contamination of subsequently transported media with possibly still present chlorine can furthermore particularly advantageously be avoided.

Since the chlorine content of the tap water that is provided from e.g. public utilities sometimes differs greatly locally or regionally, tap water can also be used in dependence on the region as the starting solution containing chlorine that is provided separately from a measurement solution in addition to the measurement solution whose chlorine content the chlorine sensor detects in regular operation The chlorine content of the tap water can already be added to the tap water by the supplier, e.g. a public utility. Alternatively or additionally, however, chlorine can also be supplied to the tap water locally, i.e. preferably as part of the water conditioning plant itself or also in its environment, for example in a clinic.

The metering in preferably takes place by means of a chlorine metering system. The local metering of chlorine (e.g. in the form of tablets) in the tap water can be used to adapt the chlorine content of the tap water as desired.

The measurement solution would in this case be the water conditioned by the water conditioning plant, preferably for the medical or pharmaceutical sector, and the starting solution containing chlorine is tap water that can be used in a targeted manner to disinfect the sensors.

This variant provides the advantage that no tank or similar storage device or provision device has to be provided for the starting solution containing chlorine. This variant further provides the advantage that the method in accordance with the invention manages without any additional consumable (e.g. chlorine bleaching lye or chlorine dioxide) that may be expensive and/or toxic or a consumable from which a fluid containing chlorine can be acquired (e.g. brine with sodium chloride). Costs can thereby be reduced, dangers avoided, and the complexity of the sensor device, the water conditioning plant, and the method in accordance with the invention can be particularly advantageously reduced.

The method is preferably carried out at predetermined time intervals. The time intervals are here preferably set such that a regrowth of a biofilm on the chlorine sensor can be prevented or at least inhibited. The method is carried out once every 24 hours, for example. Alternatively, a carrying out every 12 hours or also every 48 hours, every 4 days, or once a week is also possible.

The method is further preferably carried out automatically cyclically at predetermined time intervals, automatically in response to a specific measured value or measured value range of the chlorine sensor, or in response to an instruction by remote maintenance. The remote maintenance can here include the case of local remote maintenance, i.e. maintenance starting from a control room that is located in the environment of the sensor and/or a water conditioning plant, for example in a clinic, associated therewith.

The automation or automatic carrying out of the disinfection method of the chlorine sensor ensures an optimum function of the chlorine sensor with a minimal staff deployment. Due to the automation of the disinfection method, its regular carrying out is furthermore particularly advantageously ensured.

A water conditioning plant with which a chlorine sensor is associated carries out the method in accordance with the invention automatically or independently, that is without human intervention, for example.

Alternatively or additionally, the method can also be carried out if the measured values of the chlorine sensor fall below a specific limit value or vary within a specific range, for example because a biofilm that is produced successively reduces the sensitivity of the sensor.

A carrying out of the method can equally be initiated by remote maintenance, for example by the transmission of corresponding control data to a device carrying out the method.

It has furthermore proved to be advantageous for the carrying out of the method to be automatically documented or recorded in an electronic/digital logbook, with the recording being able to include data transmission by means of a remove connection. The digital logbook can be recorded locally in a sensor device, in the near data environment (e.g. in the control room of a clinic), or remotely (e.g. on a server or in a data cloud). The recording can include the time of the carrying out of the method, the duration, and the concentrations of the solutions used, as well as further data.

The digital logbook can preferably be accessed remotely, for example by service engineers.

The invention furthermore relates to a method for the functional monitoring of a chlorine sensor that is preferably used as part of water conditioning for medical or pharmaceutical purposes, the method comprising the steps:
  providing a starting solution containing chlorine that is provided separately from a measurement solution whose chlorine content the chlorine sensor detects;
  diluting the starting solution containing chlorine to a desired degree;
  supplying the diluted starting solution containing chlorine to the chlorine sensor, and
  determining the chlorine content of the diluted starting solution containing chlorine by means of the chlorine sensor.

The diluted starting solution containing chlorine preferably remains in/at the chlorine sensor for a suitable dwell time or exposition time after the supply. The chlorine sensor is thus exposed to the chlorine content of the diluted starting solution containing chlorine during the exposition time. The exposition time can vary between only a few seconds and several minutes.

The exposition time preferably amounts to between approximately 1 minute and approximately 10 minutes, preferably between 2 minutes and 8 minutes, in particular between 3 minutes and 7 minutes, particularly between 4 and 6 minutes. The exposition time amounts to approximately 5 minutes in accordance with a preferred embodiment.

A shorter exposition time is also conceivable, e.g. a time between 10 seconds and 1 minute, for example approximately 30 seconds, etc. is conceivable as is a longer time such as 10 to 15 minutes.

The step of diluting the starting solution containing chlorine provides the advantages already presented above of a flexible adaptation of the concentrations used to specific applications and the possible size reduction of a tank for the starting solution containing chlorine.

In accordance with an advantageous embodiment, the functional monitoring is an adjustment or a comparison, an adaptation, or a calibration of the chlorine sensor and/or the chlorine content determined by means of the monitored chlorine sensor is compared with a measured value of a different sensor or with a known chlorine content of the diluted starting solution containing chlorine.

In a variant in which a comparison or a calibration of the chlorine sensor takes place with the functional monitoring method, the comparison or the calibration is carried out by a comparison of the monitored chlorine sensor with a measured value of a different sensor or by comparison with a fluid of a known chlorine content. The sensor steepness of an evaluation unit of the chlorine sensor can here, for example, take place or be set on the basis of the aforesaid comparison.

In a particularly advantageous further development, the further chlorine sensor is a component of a further chlorine measurement device that Is brought into contact with the fluid containing chlorine for the calibration and there is data communication between the device whose component is the monitored chlorine sensor and the device whose component is the further chlorine sensor.

Since the starting solution containing chlorine can be diluted as desired, in accordance with a further advantageous embodiment a plurality of different comparison points (with different chlorine concentrations) are traveled to.

For example, the concentration of the chlorine solution relative to a first comparison could be decreased or increased as part of the method in a second comparison and the reaction of the sensor could be checked under time aspects to thus determine the response accuracy and time of the sensor. For example, a maximum permitted response time can be fixed and the measurement results of the sensor can be evaluated accordingly so that this likewise produces information on the sensor activity or its overall status.

On a reduced sensor activity or any other functional impairment of the sensor, it is possible that the response speed of the sensor is reduced and the signal output by the sensor within the maximum permitted response time thus remains behind a corresponding normal value.

The starting solution containing chlorine can also be tap water in this embodiment of the invention in dependence on the local chlorine content of the tap water. It is also conceivable that chlorine is alternatively or additionally metered into the tap water locally.

The method for the functional monitoring or calibration of the chlorine sensor is preferably carried out automatically at predetermined time intervals, automatically in response to a specific measured value or measured value range of the chlorine sensor, or in response to an instruction by remote maintenance. The remote maintenance can here include the case of local remote maintenance, i.e. maintenance starting from a control room that is located in the environment of the sensor and/or a water conditioning plant associated therewith, for example in a clinic.

The method is preferably carried out at predetermined time intervals. The time intervals are here preferably set such that a regrowth of a biofilm on the chlorine sensor can be prevented or at least inhibited. The method is carried out once every 24 hours, for example. Alternatively, a carrying out every 12 hours or also every 48 hours, every 4 days, or once a week is also possible.

The method is further preferably carried out automatically cyclically at predetermined time intervals as described above, automatically in response to a specific measured value or measured value range of the chlorine sensor, or in response to an instruction by remote maintenance. The remote maintenance can here include the case of local remote maintenance, i.e. maintenance starting from a control room that is located in the environment of the sensor and/or a water conditioning plant associated therewith, for example in a clinic.

The carrying out of the method (time, duration, solutions, etc.) and preferably also the measured values determined within the framework of the method are furthermore preferably automatically, documented/recorded in a logbook, with the recording being able to include a data transmission by means of a remote connection. The digital logbook can be recorded locally in a sensor device, in the near data environment (e.g. in the control room of a clinic), or remotely (e.g. on a server or in a data cloud). The recording can include the time of the carrying out of the method, the duration, and the concentrations of the solutions used, as well as further data.

The digital logbook can preferably be accessed remotely, for example by service engineers.

The chlorine sensor mentioned as part of the present invention is preferably a total chlorine sensor (also called an absolute chlorine sensor) that measures online.

In such preferred embodiments of the method in accordance with the invention, the chlorine content to be determined is to be understood as a total chlorine content. The total chlorine content must be strictly distinguished from the content of free chlorine. Sensors for free chlorine are substantially simpler in structure, are less expensive, and are more widespread than total chlorine sensors.

However, the demands for many medical or pharmaceutical applications with respect to freedom from chlorine cannot be detected by means of a sensor for free chlorine. The measured values to be observed frequently relate to the total chlorine content. The variants of all the methods in accordance with the invention can be particularly advantageously used for total chlorine sensors here.

A sensor that measures online is here to be understood such that the sensor is coupled into the ongoing operation of a device, e.g. of a water conditioning plant and detects measured data during operation, for example. A sensor that measures online is furthermore to be understood such that the sensor is connected to further data processing devices so that the sensor can, for example, always be controlled or can exchange data.

The present invention is generally also not restricted to chlorine sensors, but can rather, for example, also be used for the disinfection of other sensors.

A further aspect of the present invention relates to a chlorine measurement device for a water conditioning plant having a chlorine sensor configured to carry out a method in accordance with the present invention.

The chlorine measurement device has all the structural features that are required for carrying out a method in accordance with the invention, e.g. a line for the supply of water free of chlorine for diluting the starting solution containing chlorine and/or for flushing the sensor, a tank for providing a starting solution containing chlorine and optionally an interface for transmitting data to a logbook that is preferably digital/electronic. The chlorine measurement device can comprise one or more chlorine sensors, preferably total chlorine sensors.

Such a chlorine measurement device preferably has a separate tank and/or a separate line for providing a starting solution containing chlorine that differs from a measurement solution containing chlorine and is separate therefrom and to supply this solution to a chlorine sensor. In other words, such a device preferably has a line for supplying the measurement solution to the sensor and a separate line for supplying the diluted solutions containing chlorine for the disinfection and/or adjustment of the sensor.

Another aspect of the present invention relates to a system having at least one such chlorine measurement device and a water conditioning plant. The system can have an interface for transmitting data to a logbook that is preferably digital/electronic.

The chlorine measurement device can be an integral part of the water conditioning pant or can be fixedly installed with the water conditioning plant. Alternatively, the chlorine measurement device can also be designed as modular or as separable from the water conditioning plant.

The system can also comprise a plurality of chlorine measurement devices and/or a plurality of chlorine sensors to in particular be used to adjust or match a chlorine sensor to a second chlorine sensor.

Further advantages, features, and effects of the present invention result from the following description of individual embodiments of the invention with reference to the Figures. There are shown.

Figure 1:
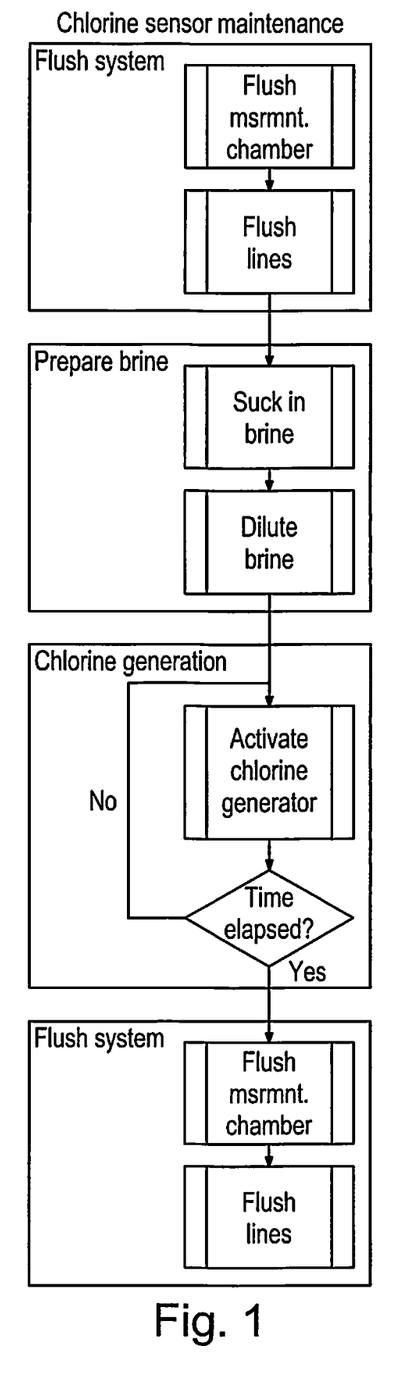
FIG. 1 schematically the flowchart of a method for the disinfection of a sensor or for maintaining a chlorine sensor.

In the method shown in FIG. 1, the measurement chamber of the chlorine sensor and the associated lines are first cleansed or flushed with water free of chlorine/low in chlorine.

If this optional step is omitted, this brings about the disadvantage that still remaining chlorine residues may change the concentration of the solutions used in an unwanted manner, whereby measurement results can be falsified or the sensor may be damaged due to the high amounts of chlorine.

In a second step, a starting solution containing chlorine is provided. Brine is specifically sucked in from a storage device in this example and is thereupon diluted with water. Alternatively to brine, a fluid containing chlorine such as chlorine bleaching lye, chlorine dioxide or similar fluids can be used.

On the dilution, the mixture of the starting solution containing chlorine and the dilution solution (e.g. water) can optionally be circulated to advantageously accelerate the mixing.

The diluted brine is thereupon supplied to the chlorine sensor, in particular to its measurement chamber. The corresponding valves are then closed to enclose the brine in the measurement chamber and a chlorine generator, for example an electrolytic chlorine generator (that is an electrolysis device), is activated to generate free chlorine ions. The step of the electrolytic provision of active chlorine can be omitted for fluids containing chlorine such as chlorine bleaching lye, chlorine dioxide, etc. since they already contain active chlorine. Devices that do not have any electrolysis device can nevertheless particularly advantageously carry out an existing functional monitoring method or disinfection method if such a fluid containing chloride having active chlorine (such as chlorine bleaching lye, chlorine dioxide) is used as the starting solution containing chlorine.

The chlorine generator is operated for a specific generation time to generate chlorine ions; the time duration can, for example, amount to between approximately 500 ms and a plurality of minutes, e.g. 5 minutes.

The chlorine generator in this example generates a solution with a concentration of approximately 1.5 mg/l free chlorine ions. As shown in the diamond in the method flowchart in FIG. 1, the chlorine generator remains activated until a predetermined generation time has elapsed or a predetermined chlorine ion concentration has been reached.

The solution containing the free chlorine ions thereupon remains in the chlorine sensor for a specific dwell time that is required for a disinfection of the chlorine sensor.

Depending on the concentration of the solution containing the free chlorine ions, the dwell time can vary between a few seconds and a plurality of minutes or even up to 30 minutes.

Once the dwell time for the disinfection has elapsed, the chlorine sensor, in particular the measurement chamber (where present) and the associated lines are cleansed or flushed of the solution containing chlorine.

A clogging of the lines by crystallization is prevented and the service life of the chlorine sensor is increased (e.g. by reduced corrosion) by the removal of the solution containing chlorine.

Figure 2:
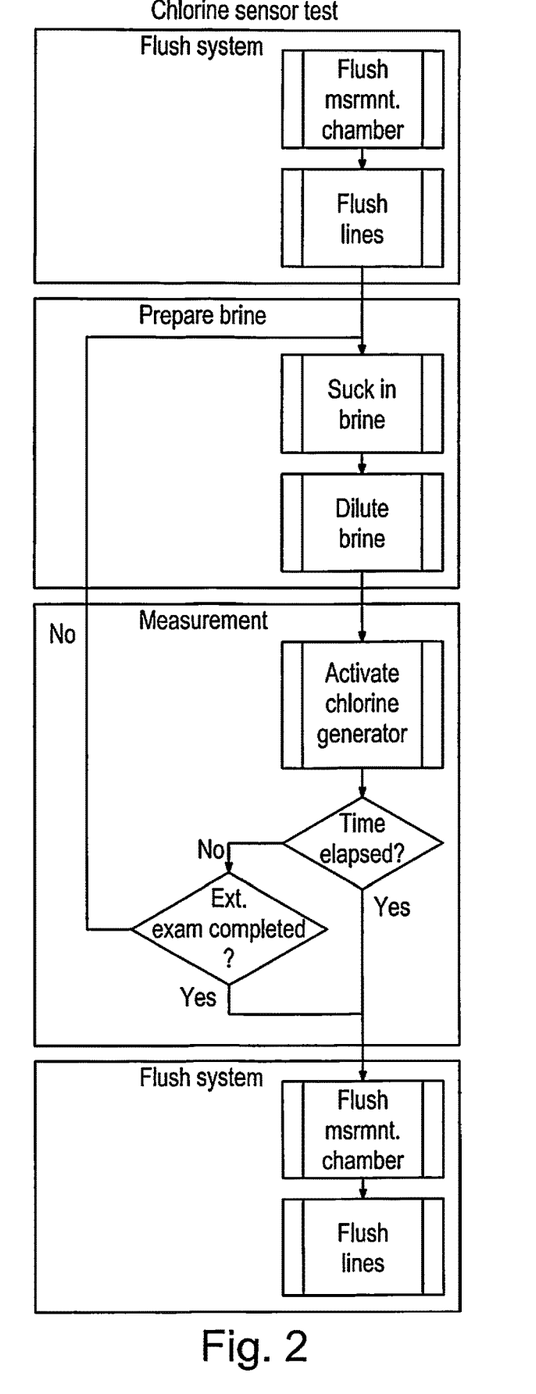
FIG. 2 schematically the flowchart of a method for the functional monitoring of a sensor.

FIG. 2 schematically shows the flowchart of a method for the functional monitoring of a sensor.

As in the method shown in FIG. 1, the measurement chamber of the chlorine sensor and the associated lines are optionally first cleansed or flushed.

If this step is omitted, this brings about the disadvantage that still remaining chlorine residues may change the concentration of the solutions used in an unwanted manner, whereby measurement results can be falsified or the sensor may be damaged due to the high amounts of chlorine.

In a second step, a starting solution containing chlorine is provided. Brine (NaCl) is specifically sucked in from a storage device and is thereupon diluted with water. Alternatively to brine, a fluid containing chlorine such as chlorine bleaching lye, chlorine dioxide or similar fluids can be used.

In the dilution, the mixture of the starting solution containing chlorine and the dilution solution (e.g. water) can optionally be circulated to advantageously accelerate the mixing.

The diluted brine is thereupon supplied to the chlorine sensor, in particular to its measurement chamber (where present). The corresponding valves are then closed to enclose the brine in the measurement chamber and a chlorine generator is activated to e.g. generate free chlorine ions by means of electrolysis. As described above, this step is not necessary on the use of a fluid containing chlorine such as chlorine bleaching lye, chlorine dioxide, or similar fluids.

The chlorine generator is operated for a specific generation time to generate chlorine ions; the time duration can, for example, amount to between approximately 500 ms and a plurality of minutes.

The chlorine generator in this example generates a solution with a concentration of approximately 1.5 mg/l free chlorine ions.

As shown in the diamond in the method flowchart in FIG. 2, the chlorine generator remains activated until a predetermined generation time has elapsed or a predetermined chlorine ion concentration has been reached.

The solution containing chlorine in this embodiment is not, however, only supplied to the chlorine sensor to be monitored, but also to a further chlorine sensor. This chlorine sensor can be a different kind of chlorine sensor, e.g. a photometric sensor, and does not have to be a sensor measuring online.

In a variant, the chlorine generator remains activated until both the chlorine sensor to be monitored and the second sensor have determined a measured value. In another variant, the generated fluid is supplied to the second sensor after the measurement of the sensor to be monitored.

The time duration for the calibration of the chlorine sensor, i.e. up to the comparison of the measured values of the chlorine sensor with the calibration value provided by the other sensor can amount to a plurality of minutes, for example approximately 30 minutes.

The two measured values are thereupon compared with one another. The sensor to be monitored is calibrated by this comparison in that the current steepness of the sensor is determined and the steepness of the chlorine sensor to be monitored is correspondingly adjusted or regulated.

The solution containing chlorine is thereupon removed from the chlorine sensor. A clogging of the lines by crystallization is prevented and the service life of the chlorine sensor is increased by the removal of the solution containing chlorine from the sensor. The advantages were described in somewhat more detail above and apply analogously.

In this embodiment of a method in accordance with the invention, the concentration of chlorine or of chlorine ions actually used is not significant. The same applies to the source of the chlorine provided.

Figure 3:
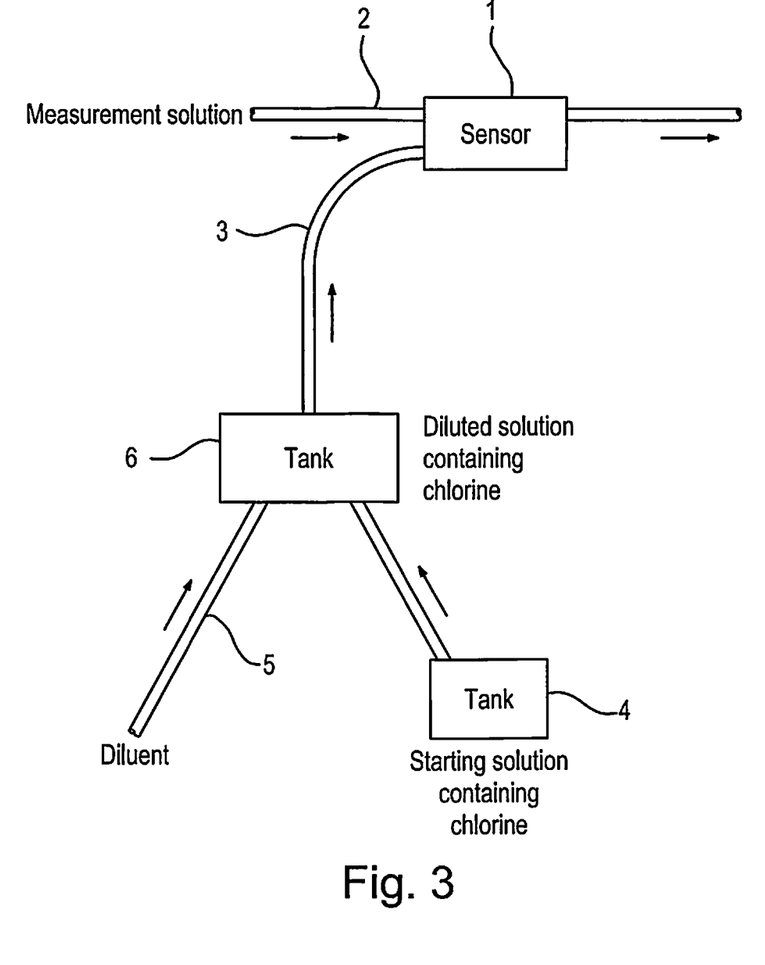
FIG. 3 a schematic view of a device in accordance with the invention.

FIG. 3 shows a schematic view of a chlorine measurement device in accordance with the invention with a chlorine sensor 1. The chlorine sensor 1 is connected to a line 2 for supplying a measurement solution. The chlorine sensor 1 is additionally connected to a separate line 3 by means of which diluted starting solution containing chlorine can be supplied to the sensor 1.

The diluted starting solution containing chlorine can leave the sensor 1 through the same line as the measurement solution, but an additional separate line can also be provided (not shown) to lead off the diluted starting solution containing chlorine.

The diluted starting solution containing chlorine is produced from a starting solution containing chlorine that is provided in a tank 4. The starting solution containing chlorine can be tap water so that the tank is not absolutely necessary.

A diluent, e.g. water, is added to the starting solution containing chlorine by means of a line 5 to dilute the starting solution containing chlorine as required. The dilution can take place in a tank 6 that can additionally act as a reservoir for the diluted starting solution containing chlorine. Such a tank 6 is optional, however.

The invention claimed is:

1. A method of disinfecting a chlorine sensor used as part of water conditioning in a medical or a pharmaceutical service, the method comprising the steps of:
   providing a starting solution containing chlorine that is provided separately from a measurement solution whose chlorine content the chlorine sensor detects,
   the measurement solution being either chlorine-free water, or at least substantially chlorine-free water, provided by a water treatment plant associated with the medical or the pharmaceutical service;
   diluting the starting solution containing chlorine to a desired degree; and
   supplying the diluted starting solution containing chlorine to the chlorine sensor.

2. The method in accordance with claim 1, wherein the supply of the diluted starting solution containing chlorine to the chlorine sensor takes place for a predetermined exposition time that is in a range of either between a few seconds and a plurality of minutes, or between approximately 10 seconds and 10 minutes, or between 1 minute and approximately 10 minutes, or between 2 minutes and 8 minutes, or between 3 minutes and 7 minutes, or between 4 and 6 minutes.

3. The method in accordance with claim 1, further comprising the step of removing the diluted starting solution containing chlorine from the chlorine sensor.

4. The method according to claim 3, wherein the step of removing the diluted starting solution containing chlorine from the chlorine sensor is a flushing of the chlorine sensor.

5. The method in accordance with claim 1, wherein the method is carried out at predetermined time intervals.

6. The method in accordance with claim 1, wherein the starting solution containing chlorine is tap water.

7. The method in accordance with claim 1, wherein the starting solution containing chlorine is provided via electrolysis from either a brine or a fluid containing chlorine, and is provided in a separate container.

8. The method according to claim 7, wherein the fluid containing chlorine is chlorine bleaching lye.

9. The method in accordance with claim 1, wherein the method is carried out either automatically cyclically at predetermined time intervals, or automatically in response to a specific measured value or measured value range of the chlorine sensor, or in response to an instruction by remote maintenance.

10. The method in accordance with claim 1, wherein data associated with the carrying out of the method is automatically recorded in either a digital or an electronic logbook, with transmission of the data of being effected via a remote connection.

11. A method of functionally monitoring a chlorine sensor used as part of water conditioning in a medical or a pharmaceutical service, the method comprising the steps of:
    providing a starting solution containing chlorine that is provided separately from a measurement solution whose chlorine content the chlorine sensor detects,
    the measurement solution being either chlorine-free water, or at least substantially chlorine-free water, provided by a water treatment plant associated with the medical or the pharmaceutical service;
    diluting the starting solution containing chlorine to a desired degree; and
    supplying the diluted starting solution containing chlorine to the chlorine sensor; and
    determining the chlorine content of the diluted starting solution containing chlorine by means of the chlorine sensor.

12. The method in accordance with claim 11, wherein the supply of the diluted starting solution containing chlorine to the chlorine sensor takes place for a predetermined exposition time that is in a range of either between a few seconds and a plurality of minutes, or between approximately 10 seconds and 10 minutes, or between 1 minute and approximately 10 minutes, or between 2 minutes and 8 minutes, or between 3 minutes and 7 minutes, or between 4 and 6 minutes.

13. The method in accordance with claim 11, wherein the functional monitoring is at least one of
    a calibration or an adjustment of the chlorine sensor, and
    the chlorine content determined of via the chlorine sensor being compared with a measured value of a different sensor or with a known chlorine content of the diluted starting solution containing chlorine.

14. The method in accordance with claim 11, wherein starting solution containing chlorine is tap water.

15. The method in accordance with claim 11, wherein the starting solution containing chlorine is produced of via electrolysis from either a brine or a fluid containing chlorine, and is provided in a separate container.

16. The method according to claim 15, wherein the fluid containing chlorine is chlorine bleaching lye.

17. The method in accordance with claim 11, wherein the method is carried out either automatically cyclically at predetermined time intervals, or automatically in response to a specific measured value or measured value range of the chlorine sensor, or in response to an instruction by remote maintenance.

18. The method in accordance with claim 11, wherein data associated with the carrying out of the method is automatically recorded in either a digital or an electronic logbook, with transmission of the data being effected via a remote connection.

19. A chlorine measurement device for a water conditioning plant, said chlorine measurement device having a chlorine sensor configured to carry out a method that includes the steps of
providing a starting solution containing chlorine that is provided separately from a measurement solution whose chlorine content the chlorine sensor detects, the measurement solution being either chlorine-free water, or at least substantially chlorine-free water, diluting the starting solution containing chlorine to a desired degree, and supplying the diluted starting solution containing chlorine to the chlorine sensor,
said chlorine measurement device comprising:
a line for supplying chlorine-free water for diluting the starting solution containing chlorine and/or for flushing the chlorine sensor;
a tank for providing the starting solution containing chlorine; and
an interface for transmitting data collected by the chlorine sensor to either a digital or an electronic logbook.

20. A system for use in a medical or a pharmaceutical service, said system comprising:
a chlorine measurement device having a chlorine sensor configured to carry out a method that includes the steps of
providing a starting solution containing chlorine that is provided separately from a measurement solution whose chlorine content the chlorine sensor detects, the measurement solution being either chlorine-free water, or at least substantially chlorine-free water, diluting the starting solution containing chlorine to a desired degree, and supplying the diluted starting solution containing chlorine to the chlorine sensor; and
a water conditioning plant that supplies the chlorine-free water or the at least substantially chlorine-free water.

* * * * *